United States Patent
El-Hennawy et al.

(10) Patent No.: US 10,583,226 B1
(45) Date of Patent: Mar. 10, 2020

(54) CATHETER LOCK SOLUTION

(71) Applicants: Adel Sayed El-Hennawy, Staten Island, NY (US); Elena Frolova, Woodmere, NY (US)

(72) Inventors: Adel Sayed El-Hennawy, Staten Island, NY (US); Elena Frolova, Woodmere, NY (US)

( * ) Notice: Subject to any disclaimer, the term of this patent is extended or adjusted under 35 U.S.C. 154(b) by 0 days.

(21) Appl. No.: 16/195,148

(22) Filed: Nov. 19, 2018

(51) Int. Cl.
*A61M 25/00* (2006.01)
*A61L 29/16* (2006.01)
*A61L 2/18* (2006.01)
*A61L 33/00* (2006.01)
*A61L 33/02* (2006.01)

(52) U.S. Cl.
CPC ......... *A61L 33/0041* (2013.01); *A61L 33/027* (2013.01); *A61M 25/0017* (2013.01); *A61L 2300/42* (2013.01); *A61M 2025/0019* (2013.01)

(58) Field of Classification Search
CPC .............. A61L 33/0041; A61L 33/027; A61L 2300/42; A61L 2/18; A61L 29/16; A61M 25/0017
See application file for complete search history.

(56) References Cited

U.S. PATENT DOCUMENTS 9,789,227 B1 * 10/2017 El-Hennawy ........... A61L 29/02
2010/0010086 A1 * 1/2010 Ash ....................... A01N 37/40
514/544

* cited by examiner

*Primary Examiner* — Sean E Conley
(74) *Attorney, Agent, or Firm* — Gearhart Law LLC

(57) ABSTRACT

The present disclosure relates to a catheter lock solution which instills into the lumen of the catheter and helps to maintain catheter patency when the catheter is not used for treatment of a patient. In particular, the present invention and its embodiments relate to a use of sodium bicarbonate solution as a catheter lock solution.

2 Claims, No Drawings

CATHETER LOCK SOLUTION

CLAIM OF PRIORITY

This application is a non-provisional application and claims no priority to any patent or patent application.

FIELD OF THE EMBODIMENTS

The field of the present invention and its embodiments relate to a catheter lock solution which instills into the lumen of the catheter and helps to maintain catheter patency when the catheter is not used for treatment of a patient. In particular, the present invention and its embodiments relate to a use of sodium bicarbonate solution as a catheter lock solution.

BACKGROUND OF THE EMBODIMENTS

Central venous catheters, originally introduced as vascular access for short-term dialysis, have been an acceptable form of permanent vascular access in some patients, particularly those with limited alternative options for vascular access. Approximately 17-18% of hemodialysis patients select tunneled cuffed catheter as long-term vascular access. Despite great advances, two major causes of catheter loss continue to plague sustained effective hemodialysis (HD) treatment: lumen clot formation (LCF) and catheter-related infection (CRI).

Some reports suggest up to 42% of catheter-related dysfunction is attributable to LCF, and a prospective study suggested that catheter-dependent HD patients have a 35% probability of developing bacteremia within three months of catheter insertion. Given the high percentage of dialysis patients who develop LCF and CRI, management that mitigates these rates may prove itself invaluable.

Multiple studies have assessed the role of catheter lock solutions for the prevention of LCF and CRI. Antibiotic lock solutions demonstrated a reduction in CRI, however, there is growing concern that their overuse enables the development of antibiotic resistance. Furthermore, it has been concluded that there is no ideal catheter lock solution to completely prevent catheter loss due to LCF and CRI.

The common method to ensure patency of the catheter is locking them with heparin at concentration of about 1000 U/mL to 10,000 U/mL. However, each hemodialysis center uses different concentration of heparin and there is no unified standard. There are downsides to utilizing heparin as a lock solution. For example, when using a heparin lock solution for indwelling venous catheter, bleeding complications have been reported and heparin was found to alter coagulation studies.

The American Diagnostic and Interventional Society of Nephrology recommends locking catheter with a low concentration (approx. 1000 U/mL) heparin solution or 4% trisodium citrate (TSC) as the low concentration heparin and TSC impart a relatively low bleeding risk for the patient.

Notwithstanding the above, even after one removes and discards the catheter lock solution, the remaining heparin attached to the wall of lumens could have an anticoagulation effect when later used. Thus, there is a need for an improved lock solution for catheters as prior solutions are not adequate.

For example, U.S. Pat. No. 8,747,911 pertains to a catheter lock composition for preventing bacterial infection having an effective amount of glycerol and sodium chloride solution. The effective amount of glycerol is between about 35-60% and sodium chloride is in a concentration range between 0.5-0.9%. The composition further includes an anticoagulant and/or an antimicrobial agent.

U.S. Pat. No. 7,132,413 pertains to compositions and methods for preventing formation of thrombosis on a liquid-contacting surface of a liquid delivery system, such as a port, catheter or port-catheter system. The liquid delivery system is connected to a patient for delivery of a liquid to the patient. The method involves contacting the surface with a thrombosis-preventing liquid containing taurolidine, taurultam or a mixture thereof, the thrombosis-preventing liquid further containing an anticoagulant agent. In an alternative embodiment, the liquid-contacting surface of the delivery system is contacted with a solution containing an anticoagulant agent, and thereafter contacted with a solution containing taurolidine, taurultam or a mixture thereof.

Various systems and methodologies are known in the art. However, their structure and means of operation are substantially different from the present disclosure. The other inventions fail to solve all the problems taught by the present disclosure. At least one embodiment of this invention is presented in the drawings below and will be described in more detail herein.

SUMMARY OF THE EMBODIMENTS

Central venous catheters, originally introduced as vascular access for short-term dialysis, have become an acceptable form of permanent vascular access. Non-tunneled and tunneled hemodialysis catheters are used for vascular access in HD patients who have no alternative access or are awaiting placement or maturation of arteriovenous fistula (AVF).

The two major causes of catheter loss are clot formation in catheter lumen and catheter related infection which includes catheter related bloodstream infection, tunnel infection, and exit site infection.

As noted above, there is currently no ideal lock solution that prevents catheter loss due clot formation in catheter lumen and catheter related infection. Previous studies successfully curbed infection rates using antibiotic lock solutions, but the liberal use of antibiotics entails potential adverse consequences upon patients and communities. Multidrug-resistant bacteria are a significant cause of sepsis, the most common cause of death in hospitalized patients, with an annual incidence of 1 million cases and 200,000 deaths in the U.S. alone (Deutschman and Tracey, 2014). The emergence and prevalence of antibiotic-resistant bacteria as an increasing cause of death worldwide should bear significant weight on the choice of a standard lock solution.

Catheter loss is associated with increased hospitalizations and high inpatient costs. Further, catheter-related bloodstream infection is one of, if not the most common, cause of nosocomial bacteremia. Catheter related infection is one of the most frequent, lethal, and costly complications of central venous catheterization. Central venous catheters are commonly associated with hospital-acquired bloodstream infections and lead to both increased intensive care unit stay and mortality.

The present invention and its embodiments relate to an improved catheter lock solution that resolves the aforementioned issues resulting from current implementations of catheter lock solutions. In a first embodiment of the present invention there is a catheter lock solution having a solution of sodium bicarbonate, the solution of sodium bicarbonate being substantially free of an antimicrobial agent, wherein the solution of sodium bicarbonate is configured to mitigate clotting of blood inside catheter lumen.

In general, the present invention succeeds in conferring the following, and others not mentioned, benefits and objectives.

It is an object of the present invention to provide an improved catheter lock solution.

It is an object of the present invention to provide an improved catheter lock solution that mitigates bleeding in a patient.

It is an object of the present invention to provide an improved catheter lock solution that maintains patency of a catheter when the catheter is not in use.

It is an object of the present invention to provide an improved catheter lock solution that contains no antimicrobial agent.

It is an object of the present invention to provide an improved catheter lock solution reduces incident of infection, bleeding, and injury to the patient.

It is an object of the present invention to provide an improved catheter lock solution that provides a uniform standard for hospitals and other care facilities.

It is an object of the present invention to provide an improved catheter lock solution that is compatible with multiple type of catheters and durations of use.

DESCRIPTION OF THE PREFERRED EMBODIMENTS

Reference will now be made in detail to each embodiment of the present invention. Such embodiments are provided by way of explanation of the present invention, which is not intended to be limited thereto. In fact, those of ordinary skill in the art may appreciate upon reading the present specification that various modifications and variations can be made thereto.

In general, catheters, whether for short or long-term use, are maintained in a patient's body and have a period of idle time. This is commonly referred to as dwell or down time, where blood in the lumen may clot. To combat this clotting tendency, various solutions may be inserted into the catheter and are referred to catheter lock solutions. These solutions prevent clotting and, in many circumstances, are also intended to prevent infection by providing an antimicrobial solution or compound that rests within catheter lumen. Lock solutions are commonly injected or otherwise inserted into the catheter lumen. However, many of the present lock solutions can impart undesirable side effects.

The present invention and its embodiments are directed to a catheter lock solution that is comprised of sodium bicarbonate, with the sodium bicarbonate being substantially free of any antimicrobial agent.

Sodium bicarbonate, at physiological concentrations, can act as a selective dissipater of the pH gradient of the proton motive force across the cytoplasmic membrane of both Gram-negative and Gram-positive bacteria.

The inhibitory effect of sodium bicarbonate has been attributed to the release of bicarbonate and its alkaline properties, each of which played a different role. At low concentrations, the inhibitory effect of sodium bicarbonate was mainly due to bicarbonate. As sodium bicarbonate increased to higher concentrations, the effect of bicarbonate reached a plateau while the alkalinating effect became the more dominant inhibitory factor. Fourier transform infrared (FTIR) analysis reveals that sodium bicarbonate reacted with the carboxyl group of some acidic amino-acid residues of protein in the spore, leads to a less orientated structure.

At physiological concentrations, bicarbonate is a selective dissipater of the pH gradient of the proton motive force across the cytoplasmic membrane of both Gram-negative and Gram-positive bacteria.

For example, sodium bicarbonate has remarkable power as an antibiotic adjuvant at physiologic concentrations, bicarbonate enhanced the activity of some antibiotics. More importantly, with respect to sepsis, bicarbonate potentiated the impact of antibiotics on four of the bacterial species identified by the World Health Organization as global health priorities. This effect was not related to an increase in pH, which was adjusted to remain physiologically normal. The WHO hypothesis for these findings was that bicarbonate interfered with the energy available to bacteria, by altering what is known as the proton motive force (PMF), an electrochemical gradient across the bacterial cell wall that bacteria harness to make energy. Bicarbonate interferes with this gradient, and this can influence how antibiotic molecules behave.

For instance, the PMF is directly related to pumps that bacteria possess in their cell membranes. As bicarbonate reduces the pH gradient, bacteria compensate by increasing the electrical gradient. Aminoglycosides' activity is more related to electrical charge, and bicarbonate enhances the entry of aminoglycosides as measured by MICs. Additionally, under normal physiologic concentrations, bicarbonate seems to make it more difficult for bacteria like $E.\ coli$ to produce energy, resulting in slower growth. Slower growth means that antibiotics that act when bacteria are actively dividing become less effective. Furthermore, their research suggested that bicarbonate modulates portions of our immune response and can have impacts on antibiotics that we fail to recognize from simple in vitro testing.

The inhibitory activity of sodium bicarbonate against some bacteria as sodium bicarbonate has been shown when sodium bicarbonate solution inhibited the growth of bacteria and yeasts in agar media model systems under certain conditions. The bicarbonate ion was identified as the probable cause of sodium bicarbonate-mediated inhibition although, in some cases, pH elevation played a significant role. Sodium chloride had been showed to have no antimicrobial effect, ruling out osmotic- and sodium-mediated mechanisms of inhibition.

Sodium bicarbonate may be a key in vivo molecule contributing to antibiotic susceptibility for a number of pathogens for the following reasons. Sodium bicarbonate serves as an abundant ionic factor present in mammalian tissues that stimulates global changes in bacterial structure, gene expression, and membrane permeability that correspond to increased susceptibility to human cationic antimicrobial peptides Antibiotic resistance is a crisis of historic proportions, and biofilms are a central part of that problem. Biofilm-related infections are inherently resistant to conventional antibiotic therapy, making them recurrent and chronic. Innovative therapeutic measures need to be developed to eradicate persistent infections. Biofilms are gelatinous masses of microorganisms capable of attaching to virtually any surface. According to the NIH, they factor into nearly 80% of all bacterial infections and are inherently resistant to antibiotics. Biofilms glom onto medical devices (e.g., heart valves, catheters, joint replacements) where they are deadly, or difficult to eradicate. Biofilms plague hospitals, and contribute greatly to our health care burden.

Sodium bicarbonate is one of the most useful anti-biofilm agent. Its alkalizing effects notwithstanding, anti-biofilm activity may be one of the important reasons for its wide ranging benefits.

EXAMPLE

In order to determine the overall safety and efficacy of using a sodium bicarbonate catheter lock solution (SBCLS) of the present invention, a study was set forth to utilize SBCLS as a means of preventing hemodialysis (HD) catheter loss due to catheter-related sepsis (CRS) and lumen clot formation (LCF). To achieve such a determination, a prospective, comparative clinical and open-label trial comparing SBCLS group to normal saline catheter lock solution (NSCLS) group who are receiving HD through catheter was performed with the results detailed herein.

The trial took place for a total period of five hundred and forty-six (546) days, and involved randomly selected patients (n=451) who were admitted to the hospital with acute kidney injury (AKI) and required HD treatment or end-stage renal disease (ESRD) on HD through catheters.

Patients with malfunctioned, clotted or infected catheter were included in the study after the new catheter was inserted. Once catheter was replaced, the patient was randomly assigned into either lock solution group (SBCLS or NSCLS).

The NSCLS group comprised two hundred and twenty-six (226) patients (50.1% of the patients) whereas the SBCLS group comprised two hundred and twenty-five (225) patients (49.9% of the patients). There were no significant differences between the two test groups based on demographic and clinical variables, with the exception of serum albumin level (p=0.006) and internal jugular vein (IJV) tunneling (p=0.002).

Primary outcome variables demonstrated statistically significant between-group differences. In the NSCLS group, 25/226 (11.1%) patients lost catheters due to LCF, 15/226 (6.6%) due to CRI, and 5/226 (2.2%) due to other malfunctions not attributable to LCF or CRI for a total of 55/226 (24.3%) due to all causes. In the SBCLS group, 1/225 (0.4%) patient lost catheters due to LCF, 1/225 (0.4%) due to CRI, and 5/225 (2.2%) due to other malfunctions not attributable to LCF or CRI for a total of 7/225 (3.1%) due to all causes.

Thus, there was a significant difference in the rate of catheter loss due to LCF, with the NSCLS group being 24.2× more likely to have catheter loss (95% CI 3.23-180.83) in comparison to the SBCLS group. There was also a significant higher rate of catheter loss due to CRS in the NSCLS group (OR 14.8, 95% CI 1.93-113.5) in comparison to the SBCLS group. Further, a non-significant difference in rates between the two groups was observed for catheter loss due to malfunction (OR 0.90, 95% CI 0.30-3.50). No serious adverse events were encountered for any of the patients.

As a result, the approach of using sodium bicarbonate as catheter lock solution was found to be a safe, effective, and statistically superior lock method in preventing hemodialysis catheter loss due to LCF and CRS. Further, sodium bicarbonate solutions are inexpensive, readily available solution in various settings and holds the potential to decrease hospitalization, length of stay, and dialysis-related costs.

Without being bound by theory, it is theorized that the present invention and its embodiments function by binding calcium and removing it from the many enzymes of the coagulation system that require it as a co-factor, thus preventing clotting.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:
1. A method of preventing loss of a hemodialysis catheter due to catheter related infection and lumen clot formation, the method comprising the steps of:
   inserting into a lumen of the hemodialysis catheter, a catheter lock solution comprising a solution of sodium bicarbonate, the solution of sodium bicarbonate being substantially free of any antimicrobial agent,
      wherein the solution of sodium bicarbonate is configured to mitigate clotting of blood;
   permitting the catheter lock solution to remain in the lumen for a first period of time; and
   removing the catheter lock solution from the lumen;
   wherein the catheter lock solution reduces hemodialysis catheter loss attributable to catheter related infection and lumen clot formation by 16.9% compared to a normal saline catheter lock solution.
2. The method of claim 1 wherein the first period of time is a duration in which the hemodialysis catheter is not in use for treatment of a patient.

* * * * *